(12) United States Patent
Fonseca et al.

(10) Patent No.: US 10,363,388 B2
(45) Date of Patent: Jul. 30, 2019

(54) SYSTEM AND METHOD FOR ENHANCING SLEEP SLOW WAVE ACTIVITY BASED ON CARDIAC CHARACTERISTICS OR RESPIRATORY CHARACTERISTICS

(71) Applicant: KONINKLIJKE PHILIPS N.V., Eindhoven (NL)

(72) Inventors: Pedro Miguel Fonseca, Borgerhout (BE); Gary Nelson Garcia Molina, Madison, WI (US); Reinder Haakma, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 271 days.

(21) Appl. No.: 15/105,635

(22) PCT Filed: Dec. 8, 2014

(86) PCT No.: PCT/IB2014/066687
§ 371 (c)(1),
(2) Date: Jun. 17, 2016

(87) PCT Pub. No.: WO2015/092606
PCT Pub. Date: Jun. 25, 2015

(65) Prior Publication Data
US 2016/0310696 A1    Oct. 27, 2016

Related U.S. Application Data

(60) Provisional application No. 61/917,523, filed on Dec. 18, 2013.

(51) Int. Cl.
*A61M 21/02* (2006.01)
*A61B 5/0205* (2006.01)
(Continued)

(52) U.S. Cl.
CPC .......... *A61M 21/02* (2013.01); *A61B 5/0077* (2013.01); *A61B 5/0205* (2013.01);
(Continued)

(58) Field of Classification Search
CPC ... A61B 5/4812; A61B 5/0077; A61B 5/0205; A61B 5/0261; A61B 5/0295;
(Continued)

(56) References Cited

U.S. PATENT DOCUMENTS 7,025,729 B2 *  4/2006  de Chazal .......... A61B 5/04325
                                                        600/508
2007/0083079 A1  4/2007  Lee et al.
(Continued)

FOREIGN PATENT DOCUMENTS

EP    1886707 A1    2/2008
EP    2644087 A1    10/2013
(Continued)

OTHER PUBLICATIONS

Mounsey, "Praecordial Ballistocardiography", British Heart Journal, 1957, pp. 1-13.
(Continued)

*Primary Examiner* — Christine H Matthews
*Assistant Examiner* — Joshua Daryl D Lannu

(57) ABSTRACT

Systems and methods for providing sensory stimuli induce and/or enhance sleep and/or slow wave neural activity of a subject during sleep. Operation of the systems and methods is based on measured information related to cardiac attributes and/or respiratory attributes of the subject, and corresponding cardiac parameters and/or respiratory parameters based thereon. Attributes may be measured and/or monitored via one or more sensors, e.g. worn on an extremity of the subject and/or placed at a distance from the subject. Sensory stimulation delivered to the subject during specific
(Continued)

targeted periods of sleep may enhance slow wave neural activity.

17 Claims, 6 Drawing Sheets

(51) Int. Cl.
    *A61B 5/0295* (2006.01)
    *A61B 5/11* (2006.01)
    *A61B 5/04* (2006.01)
    *A61B 5/00* (2006.01)
    *A61B 5/08* (2006.01)
    *A61B 5/026* (2006.01)
    *A61M 21/00* (2006.01)
    *A61N 2/00* (2006.01)

(52) U.S. Cl.
    CPC .......... *A61B 5/0261* (2013.01); *A61B 5/0295* (2013.01); *A61B 5/04001* (2013.01); *A61B 5/08* (2013.01); *A61B 5/1102* (2013.01); *A61B 5/4812* (2013.01); *A61B 5/681* (2013.01); *A61M 2021/0016* (2013.01); *A61M 2021/0022* (2013.01); *A61M 2021/0027* (2013.01); *A61M 2021/0044* (2013.01); *A61M 2205/50* (2013.01); *A61M 2205/52* (2013.01); *A61M 2230/005* (2013.01); *A61M 2230/04* (2013.01); *A61M 2230/40* (2013.01); *A61N 2/006* (2013.01)

(58) Field of Classification Search
    CPC ......... A61B 5/681; A61B 5/1102; A61B 5/08; A61B 5/04001; A61M 21/02; A61M 2021/0016; A61M 2021/0022; A61M 2021/0027; A61M 2021/0044; A61M 2205/50; A61M 2230/04; A61M 2230/40; A61M 2205/52; A61M 2230/005; A61N 2/006
    See application file for complete search history.

(56) References Cited

U.S. PATENT DOCUMENTS

| | | |
|---|---|---|
| 2008/0234785 A1 | 9/2008 | Nakayama et al. |
| 2009/0131803 A1 | 5/2009 | Heneghan et al. |
| 2010/0087701 A1* | 4/2010 | Berka .................. A61M 21/02 600/27 |
| 2010/0131028 A1 | 5/2010 | Hsu et al. |
| 2013/0046151 A1 | 2/2013 | Bsoul et al. |
| 2014/0378857 A1 | 12/2014 | Masuda et al. |

FOREIGN PATENT DOCUMENTS

| | | |
|---|---|---|
| JP | 2011015887 A | 1/2011 |
| JP | 2013128659 A | 7/2013 |
| WO | 2005055802 A2 | 6/2005 |
| WO | 2006004230 A1 | 1/2006 |
| WO | 2006054210 A1 | 5/2006 |
| WO | 2007143535 A2 | 12/2007 |
| WO | 2008096307 A1 | 8/2008 |
| WO | 2008104918 A1 | 9/2008 |
| WO | 2010107928 A2 | 9/2010 |
| WO | 2011114333 A2 | 9/2011 |
| WO | 2011132118 A2 | 10/2011 |
| WO | 2012095783 A1 | 7/2012 |
| WO | 2012131589 A2 | 10/2012 |
| WO | 2012164453 A1 | 12/2012 |
| WO | 2013179189 A1 | 12/2013 |

OTHER PUBLICATIONS

Achermann et al, "A Model of Human Sleep Homeostasis Based on EEG Slow-Wave Activity: Quantitative Comparison of Data ND Simulations", Brain Research Bulletin, vol. 31, No. 1-2, 1993, pp. 97-113.

Merica et al, "State Transitions Between Wake and Sleep, and Within the Ultradian Cycle, with Focus on the Link to Neuronal Activity", Sleep Medicine Reviews, vol. 8, 2004, No. 6, pp. 473-485.

Merica et al, "A Neuronal Transition Probability Model for the Evolution of Power in the Sigma and Delta Frequency Bands of Sleep EEG", Physiology & Behavior, vol. 62, No. 3, 1997, pp. 585-589.

Long et al, "Respiration Amplitude Analysis for REM and NREM Sleep Classification", 35th Annual International Conference of the IEEE EMBS, 2013, pp. 5017-5020.

Redmond et al, "Cardiorespiratory-Based Sleep Staging in Subjects With Obstructive Sleep Apnea", IEEE Transactions on Biomedical Engineering, vol. 53, No. 3, 2006, pp. 485-496.

Yilmaz et al, "Sleep Stage and Obstructive Apneaic Epoch Classification Using Single-Lead ECG", Biomedical Engineering Online, (;39, 2010, pp. 1-14.

Teich et al, "Heart Rate Variability: Measures and Models", ARAXIV:Physics Preprint Physics, 2000, pp. 1-84.

Madalena et al, "Multiscale Entropy Analysis of Complex Physiologic Time Series", Physical Review Letters, 'vol. 89, No. 6, 2002, pp. 1-4.

Camm et al, "Heart Rate Variability: Standards of Measurement, Physiological Interpretations, and Clinical Use", Circulation, vol. 93, 1996, pp. 1043-1065.

Richman et al, "Physiological Time-Series Analysis Using Approximate Entropy and Sample Entropy", AM Journal of Physiol Heart Circ Physiol, vol. 278, 2000, pp. H2039-H2049.

Mendez et al, "Time-Varying Analysis of the Heart Rate Variability During REM and Non REM Sleep Stages", Engineering in Medicine and Biology Society, 2006, pp. 3576-3579.

Kantelhardt et al, "Detecting Long-Range Correlations With Detrended Fluctuation Analysis", Physica A, vol. 295, 2001, pp. 441-454.

Schramm et al, "Quantitative Measurement of Sleep Quality Using Cardiopulmonary Coupling Analysis: A Retrospective Comparison of Individuals With and Without Primary Insomnia", Sleep Breath, vol. 17, pp. 713-721.

Adnane et al, "Automatic Sleep-Wake Stages Classifier Based ONECG", ICROS-SICE International Joint Conference, 2009, pp. 493-498.

Suhrbier et al, "Cardiovascular Regulation During Sleep Quantified by Symbolic Coupling Traces", CHAOS, vol. 20, 2010, pp. 045124-1-045124-7.

* cited by examiner

SYSTEM AND METHOD FOR ENHANCING SLEEP SLOW WAVE ACTIVITY BASED ON CARDIAC CHARACTERISTICS OR RESPIRATORY CHARACTERISTICS

CROSS-REFERENCE TO PRIOR APPLICATIONS

This application is the U.S. National Phase application under 35 U.S.C. § 371 of International Application Ser. No. PCT/IB2014/066687, filed on 8 Dec. 2014, which claims the benefit of U.S. Application Ser. No. 61/917,523, filed on 18 Dec. 2013. These applications are hereby incorporated by reference herein.

BACKGROUND

1. Field

The present disclosure pertains to a system and method for providing sensory stimulation to a subject during sleep to enhance a certain type of neural activity. The proper time or interval to provide stimulation is determined based on output signals generated by one or more sensors that convey information related to a cardiac attribute and/or a respiratory attribute.

2. Description of the Related Art

Systems for monitoring sleep are known. Typical systems for monitoring sleep include an electroencephalogram (EEG) cap worn on the head of a user during sleep. The EEG cap decreases the comfort level of the user which may interrupt sleep. Sensory stimulation during sleep is known. Sensory stimulation during sleep is often applied in a closed-loop manner by using the EEG signals as reference.

SUMMARY

Accordingly, one or more aspects of the present disclosure relate to a system configured to provide sensory stimuli to enhance sleep of a subject. The system comprises one or more sensory stimulators, one or more sensors, and one or more processors. The one or more sensory stimulators are configured to provide sensory stimuli to the subject. The one or more sensors are configured to generate output signals conveying information related to one or both of a cardiac attribute and a respiratory attribute of the subject during sleep. The one or more processors are configured to execute computer program components. The computer program components include a parameter component, a neural component, and a control component. The parameter component is configured to determine one or both of a cardiac parameter and a respiratory parameter of the subject. Such a determination is based on the generated output signals from the one or more sensors. The neural component is configured to determine whether the subject generates a target level of neural activity based on the determination by the parameter component. The control component is configured to control the one or more sensory stimulators to provide the sensory stimuli to enhance sleep and/or slow wave activity in the subject. Operation of the control component is based on determinations by the neural component. In some embodiments, an amount, intensity, magnitude, power, and/or level of slow wave activity corresponds to the level of neural activity of a subject in the 0.5-4.0 Hz band.

Yet another aspect of the present disclosure relates to a method for providing sensory stimuli to enhance sleep and/or slow wave activity of a subject during sleep. The method includes generating output signals conveying information related to one or both of a cardiac attribute and a respiratory attribute of the subject during sleep; determining one or both of a cardiac parameter and a respiratory parameter of the subject based on the generated output signals; determining whether the subject generates a target level of neural activity based on the determination of one or both of the cardiac parameter and the respiratory parameter; and controlling the one or more sensory stimulators to provide sensory stimuli to enhance sleep and/or slow wave activity in the subject based on the determination whether the subject generates the target level of neural activity (in a particular band of frequencies).

Still another aspect of present disclosure relates to a system configured to provide sensory stimuli to enhance sleep and/or slow wave activity of a subject during sleep. The system includes means for providing sensory stimuli to the subject; means for generating output signals conveying information related to one or both of a cardiac attribute and a respiratory attribute of the subject during sleep; first means for determining one or both of a cardiac parameter and a respiratory parameter of the subject based on the generated output signals; second means for determining whether the subject generates a target level of neural activity based on determinations by the first means of determining; and means for controlling the means for providing sensory stimuli to the subject to enhance sleep and/or slow wave activity in the subject based on determinations by the second means.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
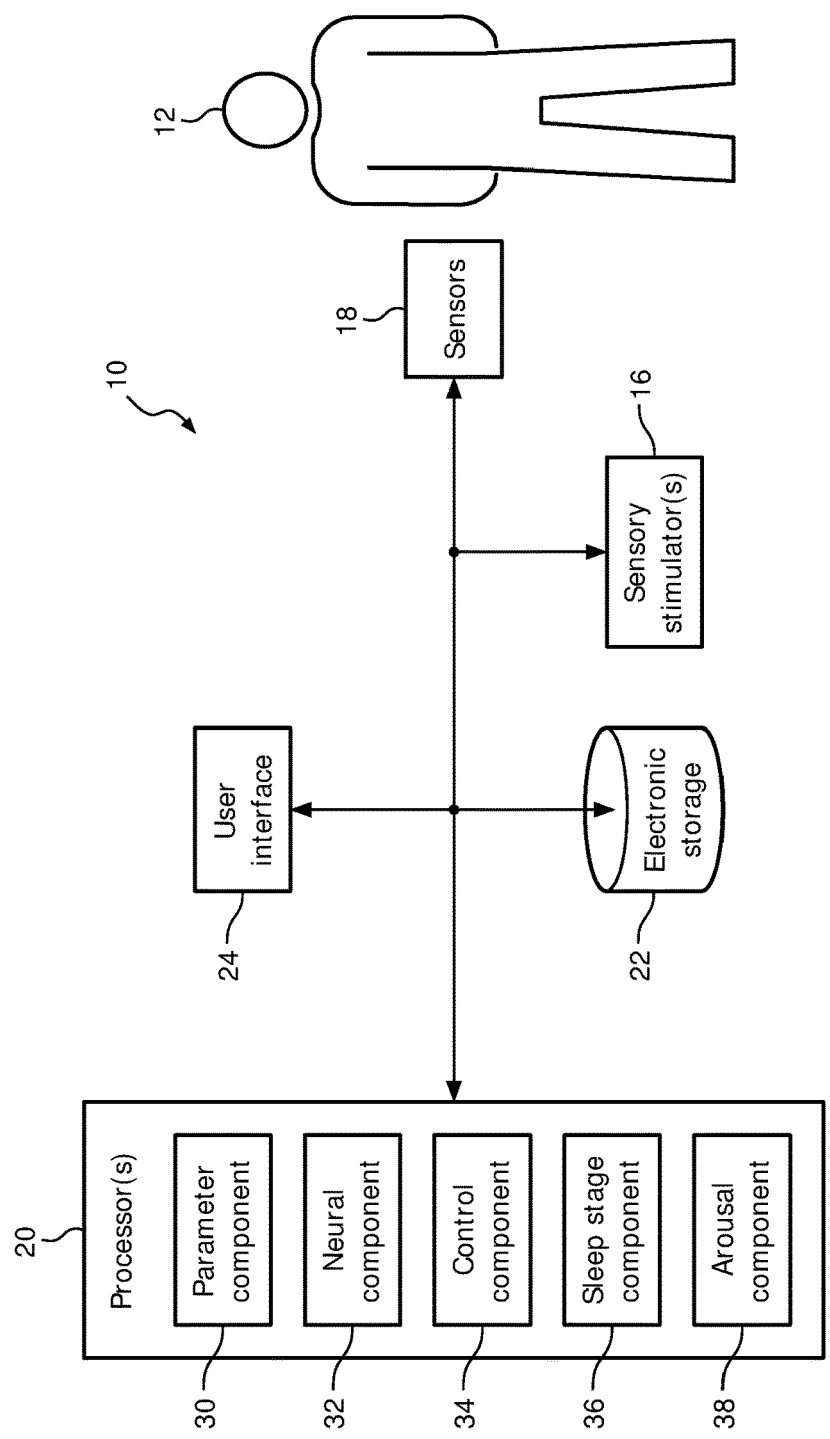
FIG. 1 is a schematic illustration of a system configured to manage a current sleep session of a subject based on output signals generated by one or more sensors that convey information related to a pulse rate and/or a blood volume of the subject during the current sleep session.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to provide sensory stimulation to a subject 12. The sensory stimulation may enhance sleep of subject 12, e.g. by enhancing the restorative power of sleep. In some embodiments, system 10 may be configured to enhance slow wave activity (SWA) of a subject during sleep. In some embodiments, system 10 may comprise one or more of a sensory stimulator 16, a sensor 18, a processor 20, electronic storage 22, a user interface 24, and/or other components. Cardio-respiratory signals may provide a correlate of neural activity that is close to the information provided by an EEG. The timing of the delivery of sensory stimulation may be based on the (estimated) level of neural activity.

In some embodiments, system 10 may be configured to detect a particular sleep stage (based on one or more cardiac attributes and/or one or more respiratory attributes of subject 12) and use such detections as a basis for the provision of sensory stimulation. Alternatively, and/or simultaneously, in some embodiments, system 10 may be configured to detect and/or determine slow wave sleep, and provide sensory stimulation based thereon, e.g. without determining a current sleep stage. Alternatively, and/or simultaneously, in some embodiments, system 10 may be configured to detect and/or determine a particular autonomic state of subject 12, and provide sensory stimulation based thereon, e.g. without determining a current level of neural activity of subject 12.

System 10 is configured to determine the level of neural activity of subject 12, for example during sleep. The level of neural activity may be determined based on one or more cardiac parameters and/or one or more respiratory parameters. These parameters may be based on output signals generated by one or more sensors 18. System 10 is configured to deliver sensory stimulation (e.g., auditory stimulation) based on output signals generated by sensor 18 that convey information related to one or both of a cardiac attribute and a respiratory attribute of subject 12, and/or other information during a current sleep session. System 10 is configured such that the delivery of sensory stimulation during sleep induces and/or enhances slow wave activity in subject 12. The delivery of the sensory stimulation may be timed to correspond to sleep stages (likely to be) associated with slow wave activity.

Figure 2:
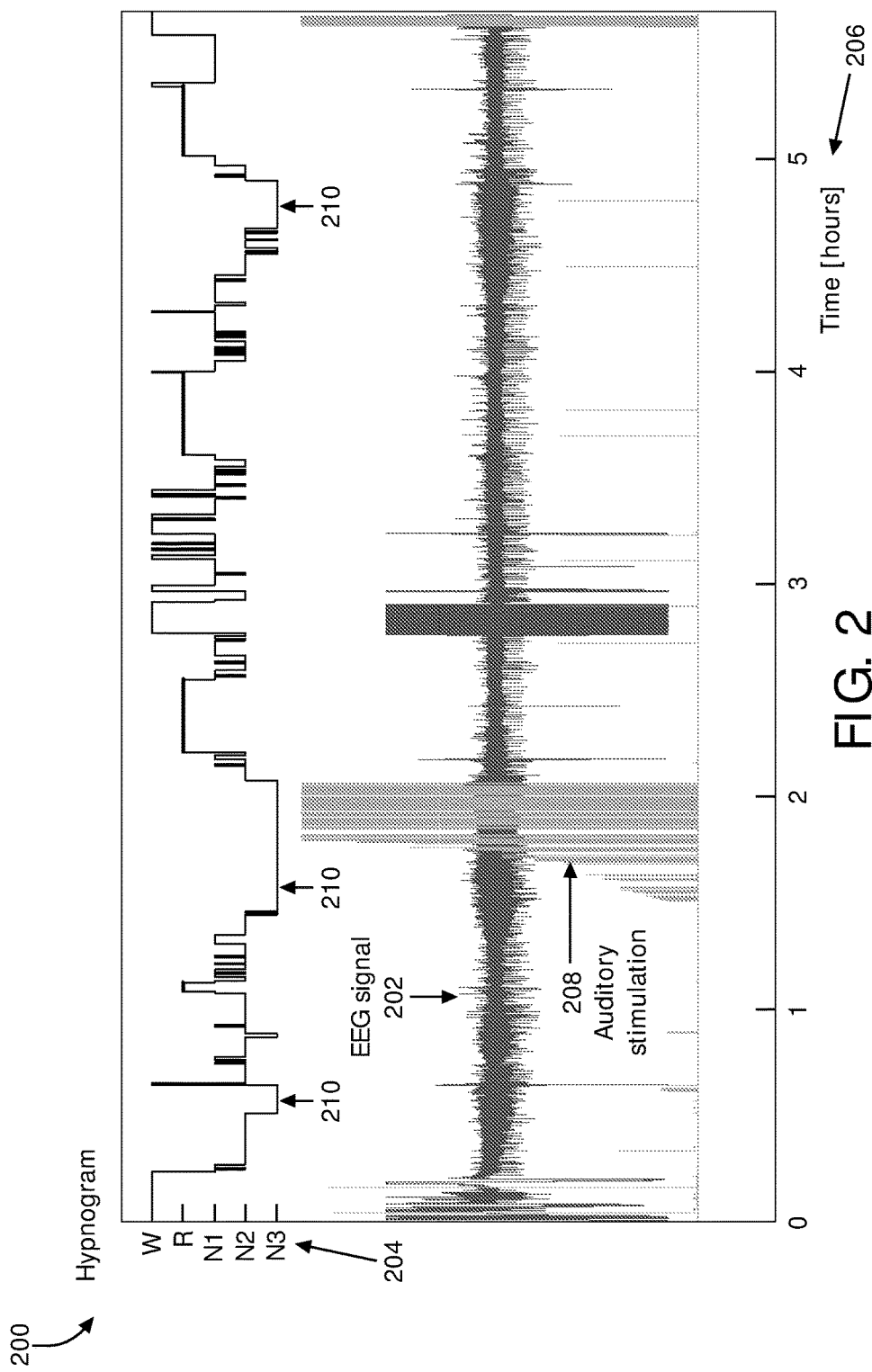
FIG. 2 illustrates a hypnogram and an EEG signal.

The term "slow wave sleep" may be used to refer to sleep of a subject during which the amount, intensity, magnitude, power, and/or level of neural activity in a particular band of frequencies (e.g. 0.5-4 Hz) is at and/or below a particular target level of neural activity. Neural activity may be observed by way of, e.g., an electro-encephalogram (EEG). FIG. 2 illustrates hypnogram 200 and EEG signal 202. Hypnogram 200 illustrates sleep stage 204 variation over time 206 for a sleep session of a subject. The sleep stages may include wakefulness (W), rapid eye movement (R), and/or non-rapid eye movement stage N1, stage N2, or stage N3 sleep. In some embodiments, slow wave sleep and/or slow wave activity may correspond to stage N3 sleep. In some embodiments, stage N2 and/or stage N3 sleep may be slow wave sleep and/or correspond to slow wave activity. In the non-limiting example shown in FIG. 2, auditory stimulation 208 is timed for delivery during (sufficiently extensive) periods of slow wave sleep 210. In some embodiments, slow waves may not be present throughout an entire N3 period, for example, but it may be significantly more likely that such slow waves are present during N3. Slow waves may also be present (although to a lesser extent) during N2, for example. An EEG signal is typically generated via a headset worn by a subject during sleep. Wearing an EEG monitoring system on the head during sleep may be cumbersome and disrupt the sleep of the subject. The system described herein may alleviate the need for wearing a headset and/or any use of an EEG monitoring system during sleep.

In some embodiments, the amount, intensity, magnitude, power, and/or level of neural activity in other bands of frequencies (e.g. the beta band between 15-30 Hz, the spindle band between 11-15 Hz, etc.) may be used by system 10. In some embodiments, ratios between two or more bands may be used, e.g. by neural component 30.

Returning to FIG. 1, sensory stimulator 16 is configured to provide sensory stimuli to subject 12. Sensory stimulator 16 is configured to provide sensory stimuli to subject 12 prior to a sleep session, during a sleep session, and/or at other times. For example, sensory stimulator 16 may be configured to provide sensory stimuli to subject 12 during slow wave sleep in the current sleep session. Sensory stimulator 16 may be configured to provide sensory stimulation to subject 12 during the current sleep session to induce, enhance, and/or adjust slow wave activity in subject 12. In some embodiments, sensory stimulator 16 may be configured such that adjusting includes increasing, decreasing, and/or other adjustment of slow wave activity in subject 12.

In some embodiments, sensory stimulator 16 may be configured to induce and/or adjust slow wave activity through non-invasive brain stimulation and/or other methods. Sensory stimulator 16 may be configured to induce, enhance, and/or adjust slow wave activity through non-invasive brain stimulation using sensory stimuli. The sensory stimuli may include odors, sounds, visual stimulation, touches, tastes, and/or other stimuli. For example, sensory stimulator 16 may be configured to induce, enhance, and/or adjust slow wave activity via auditory stimulation of subject 12. Examples of sensory stimulator 16 may include one or more of a music player, a tone generator, a collection of electrodes, a unit to deliver vibratory stimulation (also known as somato-sensory stimulation), a coil generating a magnetic field to directly stimulate the brain's cortex, light generators, a fragrance dispenser, and/or other devices. In some embodiments, sensory stimulator 16, sensors 18, and/or other components of system 10 may be integrated into a single device. For example, sensory stimulator 16 may be incorporated into a wristband worn by subject 12 during sleep that also includes sensor 18. In some embodiments, sensory stimulator 16 may be configured to deliver vibratory stimulation to the wrist of subject 12. The number of sensory stimulators in system 10 is not limited by any of the figures.

Sensor 18 is configured to generate output signals conveying information related to one or more cardiac attributes and/or one or more respiratory attributes of subject 12, e.g. during sleep. The number of sensors in system 10 is not limited by any of the figures. For example, system 10 may include multiple sensors 18. System 10 may include different types of sensors 18. Sensors 18 may include one or more of optical sensors (e.g. using photoplethysmography), ballistocardiographic sensors (e.g. based on accelerometers, piezoelectric sensors, and/or strain gauges installed e.g. in or under a mattress), Doppler radar, (in-ear) electrodes, (infrared) cameras, and/or other sensors. In some embodiments, sensor 18 may include an in-ear photoplethysmographic sensor.

Cardiac attributes may include heart rate, cardiac interbeat intervals (IBIs), and/or other cardiac attributes, e.g. cardiac attributes related to output signals generated by sensor 18. Respiratory attributes may include respiratory rate/frequency, respiratory effort, respiratory timing, and/or other respiratory attributes, e.g. respiratory attributes related to output signals generated by sensor 18.

In some embodiments, sensor 18 may be configured to maintain the comfort of subject 12 during sleep such that sleep is not interrupted by discomfort caused by sensor 18. Sensor 18 may include an optical sensor 40 (shown in FIG. 3), a camera 50 (shown in FIG. 4), an accelerometer, and/or other sensors configured to measure movement and/or other characteristics of subject 12. Sensor 18 may be configured to be carried (e.g., worn) by an extremity of subject 12, placed at a distance from subject 12, and/or configured in other ways. Sensor 18 may comprise one or more sensors that generate output signals conveying information indirectly. Sensor 18 may generate output signals conveying information related to movement of subject 12, respiration of subject 12, and/or other characteristics of subject 12. For example, sensor 18 may include an accelerometer such that sleep may be analyzed using actigraphy signals. The accelerometer may be integrated with sensor 18 as a single device and/or may be configured to be a stand-alone component of system 10. In some embodiments, the accelerometer may be integrated into a bracelet and/or a wrist band, for example, worn by subject 12.

Figure 3:
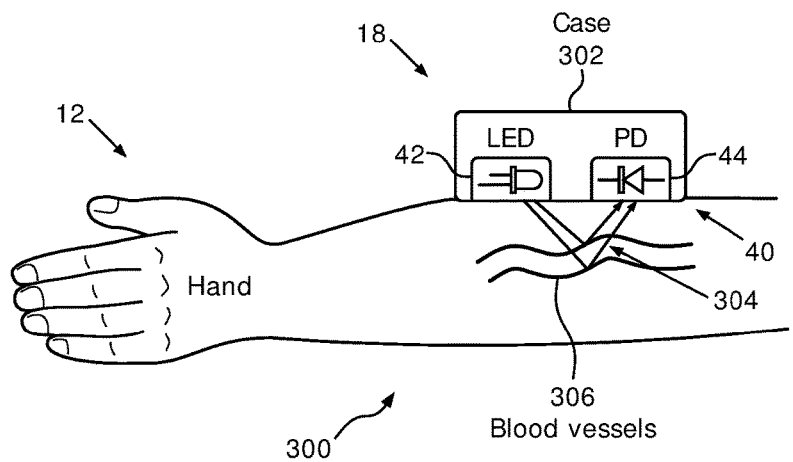
FIG. 3 illustrates an optical sensor configured to be worn on the wrist of a subject.

By way of a non-limiting example, FIG. 3 illustrates an embodiment of sensor 18 wherein sensor 18 includes optical sensor 40 and is configured to be worn on the wrist 300 of subject 12. As shown in FIG. 3, optical sensor 40 includes light source 42, photodiode assembly 44, and/or other components. In some embodiments, light source 42 and/or photodiode assembly 44 may be housed by a housing (e.g., case 302) coupled to the extremity of subject 12, coupled with a band of flexible material worn around an extremity of subject 12, removably coupled to an extremity of subject 12 via an adhesive, and/or carried by an extremity of subject 12 via other mechanisms. Light 304 from light source 42 may be scattered and/or absorbed by blood in blood vessels 306. Photodiode assembly 44 may generate output signals indicating an amount of light from light source 42 not absorbed by the blood in blood vessels 306 in wrist 300.

In some embodiments, optical sensor 40 is configured such that the extremity of subject 12 includes an arm, a leg, a wrist, a finger, an ankle, a toe, and/or other extremities of subject 12. In some embodiments, optical sensor 40 may be incorporated into a clamp and/or other devices configured to removably couple with an extremity of subject 12. Optical sensor 40 may be configured to remain in a position facing the skin of subject 12, e.g. throughout the sleep session. In some embodiments, optical sensor 40 may be configured such that the output signals are transmitted wirelessly.

Light source 42 is configured to light an area of skin on an extremity of subject 12. In some embodiments, light source 42 may be a light emitting diode (LED). The LED may emit monochromatic light. In some embodiments, the monochromatic light is green. In some embodiments, the monochromatic light is a color other than green. In some embodiments, the light is not monochromatic. At least some of the emitted light may be scattered and/or absorbed by blood in blood vessels 306 of the area of skin. Photodiode assembly 44 is configured to generate output signals indicating an amount of light 304 from the light source not absorbed by the blood in the blood vessels in the area of skin. The amount of light 304 not absorbed is related to one or more cardiac attributes and/or respiratory attributes, and/or other characteristics of subject 12. By way of non-limiting example, when the heart of subject 12 pulsates, the blood volume of the blood vessels in the skin changes (as well as other electrophysiological changes may occur) and the output signals from photodiode 44 reflect this change or other changes to indicate more or less absorbed light.

Figure 4:
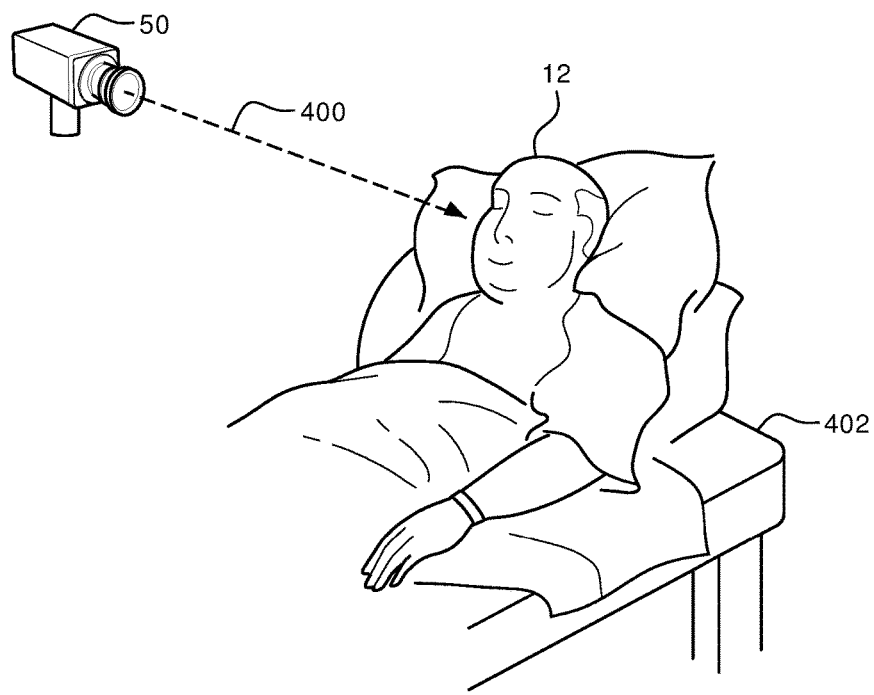
FIG. 4 illustrates a camera that is configured to be placed at a distance from a subject and directed toward an area of the skin of the body of the subject.

As shown in FIG. 4, camera 50 is configured to be placed at a distance 400 from subject 12 and directed toward an area of the skin of the body of subject 12. In some embodiments, the area of the skin of the body of subject 12 is the face of subject 12. In some embodiments, camera 50 may be directed at subject 12 while subject 12 sleeps in a bed 402, for example. Camera 50 is configured to generate output signals related to changes in the color of the skin in the area of the body of subject 12 toward which the camera is directed. The color of the skin may be related to one or more physiological attributes of subject 12, and/or other characteristics of subject 12. For example, changes in the color of the skin may indicate changes in the volume of blood in the blood vessels in the monitored area, for example. In some embodiments, camera 50 may be a vital signs camera. In some embodiments, camera 50 may be a camera of a mobile device associated with subject 12 and/or other users. In some embodiments camera 50 may utilize infrared light to generate output signals related to the changes in skin color. Utilizing infrared light may decrease the likelihood that the user wakes up during the sleep session. In some embodiments, an infrared light source is placed next to the bed, which illuminates the user's body and can then enhance the signal received by the camera. In some embodiments, system 10 may be configured such that the output signals from camera 50 are transmitted wirelessly and/or via wires.

Returning to FIG. 1, although sensor 18 is described herein at a location carried by an extremity of subject 12 or located at a distance from subject 12, this is not intended to be limiting. Sensor 18 may include one or more of the different types of sensors disposed in a plurality of locations. For example, multiple sensors 18 may be disposed on multiple limbs of subject 12. An optical sensor may be disposed on an extremity of subject 12 while a camera is disposed at a distance from subject 12. In some embodiments, multiple cameras may be disposed at multiple distances from subject 12.

Processor 20 is configured to provide information processing capabilities in system 10. As such, processor 20 may comprise one or more of a digital processor, an analog processor, and a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16), or processor 20 may represent processing functionality of a plurality of devices operating in coordination.

As shown in FIG. 1, processor 20 is configured to execute one or more computer program components. The one or more computer program components may comprise one or more of a parameter component 30, a neural component 32, a control component 34, a sleep stage component 36, an arousal component 38, and/or other components. Processor 20 may be configured to execute components 30-38 by software; hardware; firmware; some combination of software, hardware, and/or firmware; and/or other mechanisms for configuring processing capabilities on processor 20.

It should be appreciated that although components 30-38 are illustrated in FIG. 1 as being co-located within a single processing unit, in embodiments in which processor 20 comprises multiple processing units, one or more of components 30-38 may be located remotely from the other components. The description of the functionality provided by the different components 30-38 described below is for illustrative purposes, and is not intended to be limiting, as any of components 30-38 may provide more or less functionality than is described. For example, one or more of components 30-38 may be eliminated, and some or all of its functionality may be provided by other components 30-38. As another example, processor 20 may be configured to execute one or more additional components that may perform some or all of the functionality attributed below to one of components 30-38.

Determinations by parameter component 30, neural component 32, sleep stage component 36, and/or arousal component 38 may include approximations, estimations, probabilities, and/or other ways to make decisions. As used herein, the term "determine" may be interpreted to mean "measure, analyze, process, approximate, estimate, and/or otherwise decide."

Parameter component 30 is configured to determine one or more cardiac parameters and/or one or more respiratory parameters. Determinations by parameter component 30 may be based on output signals from sensors 18. The cardiac and respiratory parameters described herein have been experimentally determined to be useful in discriminating between sleep stages. By way of non-limiting example, in some experiments, validation used a (2-class Bayesian) linear discriminant classifier. Alternatively, and/or simultaneously, the cardiac and respiratory parameters described herein have been experimentally determined to be useful in discriminating between different levels/intensities of (slow wave) neural activity (e.g. without measuring neural activity directly). Alternatively, and/or simultaneously, the cardiac and respiratory parameters described herein have been experimentally determined to be useful in discriminating between different autonomic states. The discriminatory power (e.g. sensitivity, specificity, and/or precision) of these parameters may increase upon combination. In some embodiments, discriminatory power may be represented, for each attribute/parameter, by its absolute standardized mean distance (ASMD), based on the standardized mean difference (SMD). SMD expresses the difference between classes relative to the variability.

The one or more cardiac parameters may include cardiac interbeat intervals (IBIs), a pulse rate metric, a blood volume metric, windowed de-trended fluctuation analysis (DFA) coefficients of RR interval series, mean absolute deviation of the RR intervals, standard deviation of RR intervals, sample entropy of the RR intervals time series, value range of RR intervals, power of heart rate variability (HRV) spectrum at the respiratory frequency (in the frequency domain), low frequency HRV power, approximate entropy of respiratory effort amplitude peaks, ratio between low and high HRV power, module of the HF power of HRV, high frequency HRV power, scaling exponent of DFA over all time scales, very low frequency HRV power, phase coordination between RR intervals and respiratory frequency (using only IBIs), and/or other parameters. The pulse rate metric may be related to heart rate variability (HRV), and/or other pulse rate metrics. Heart rate variability may be defined as the variation in the time interval between heartbeats. Blood volume metric may be related to low frequency changes in blood volume in about the 0.04-0.30 Hz range, for example, and/or other blood volume metrics.

The one or more respiratory parameters may include a standardized median trough respiratory amplitude, a standardized mean trough respiratory amplitude, standard deviation of the respiratory frequency over a sliding window, approximate entropy of respiratory effort trough amplitudes, mean breath-by-breath correlation, ratio between the low and high frequency band power of respiratory effort, high frequency band power of respiratory effort, and/or other respiratory parameters. For any parameter using respiratory trough some embodiment may use respiratory peak instead, and vice versa. In some embodiments, respiratory parameters may use and/or be based on information pertaining to both respiratory trough and respiratory peak.

In some embodiments, parameter component 30 may be configured to determine parameters based on both at least one cardiac attribute and at least one respiratory attribute. For example, determined parameters may include phase coordination between RR intervals and respiratory effort. Combinations and/or transformations of cardiac and/or respiratory parameters (including but not limited to aggregation, statistical manipulations, low-pass filtering, high-pass filtering, and/or combinations thereof) are considered within the scope of this disclosure.

In some embodiments, parameter component 30 may be configured to determine one or more arousal metrics based on the generated output signals. Arousal metrics may indicate a level of wakefulness in subject 12, and/or a likelihood that subject 12 will wake up very soon.

In some embodiments, parameter component 30 may be configured to determine one or more autonomic parameters based on the generated output signals. Autonomic parameters may indicate a current (estimated and/or determined) autonomic state of subject 12 and/or may indicate or correspond to a particular level of neural activity.

Figure 5:
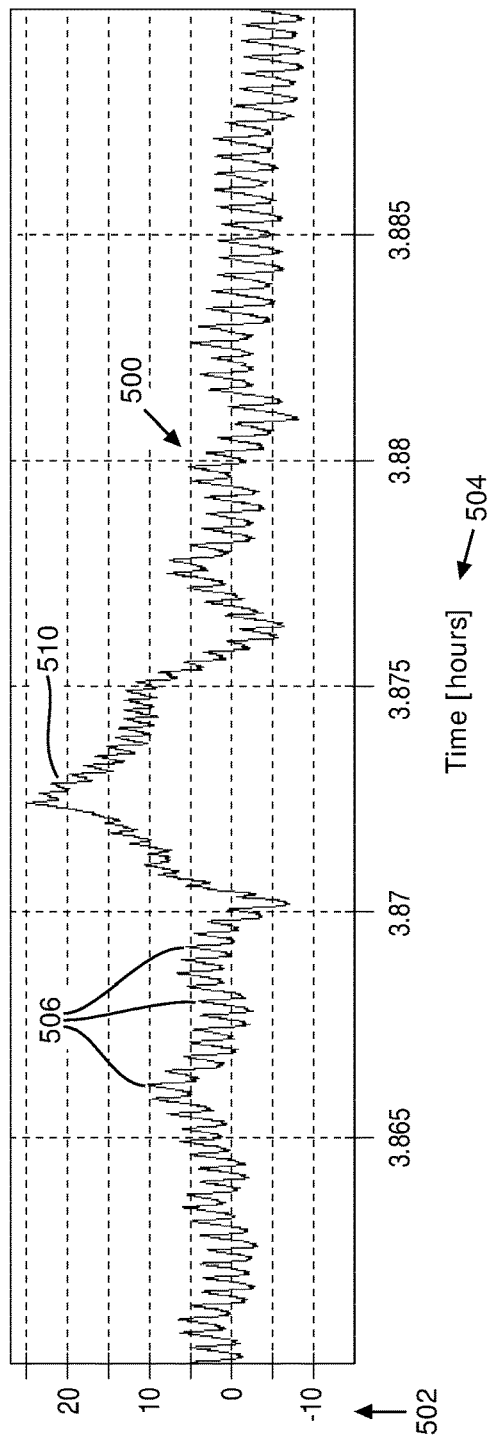
FIG. 5 illustrates high frequency variation that corresponds to the pulse rate of a subject.

FIG. 5 illustrates an example of an output signal 500 from sensor 18 (shown in FIG. 1). The characteristics (e.g., frequency, amplitude, baseline variations, peak to peak time intervals, etc.) of output signal 500 may be used by parameter component 30 (shown in FIG. 1) to determine the one or more cardiac parameters and/or other information. Output signal 500 may illustrate a signal representing changes in blood volume, for example, generated by optical sensor 40 (shown in FIG. 3), camera 50 (shown in FIG. 4), and/or other sensors. The signal strength 502 of output signal 500 varies over time 504. Peaks 506 in signal 500 appear approximately every second in this example and may represent heart beats of a subject (e.g., subject 12). Parameter component 30 may determine heart rate variability, for example, based on peaks 506.

Referring to FIG. 1, neural component 32 is configured to determine whether subject 12 generates a target level of neural activity based on one or more determinations by parameter component 30. The target level of neural activity may be selected such that an amount, intensity, magnitude, power, or level above the target level is deemed inappropriate to be considered slow wave sleep, and such that an amount, intensity, magnitude, power, or level at and/or below the target level is deemed appropriate to be considered slow wave sleep. In some embodiments, determinations by neural component 32 are performed by estimating an intensity of slow wave neural activity of subject 12. Estimation accuracy may improve by using multiple different cardiac parameters and/or respiratory parameters, as determined by parameter component 30, in conjunction. In some embodiments, neural component 32 is configured to detect a neural state of subject 12 based on one or more determinations by parameter component 30.

In some embodiments, determinations by neural component 32 may be based on one or more autonomic parameters.

Arousal component 38 is configured to detect arousals of subject 12 and/or determine an arousal metric indicating a level of wakefulness in subject 12. For example, Arousals may be detected based on one or more arousal metrics. By way of non-limiting example, an arousal metric may be determined based on movement of subject 12. Movement of subject 12 may be determined based on high frequency noise in the cardiac signals from sensors 18, movement of subject 12 determined via camera 50, movement of subject 12 determined via the accelerometer, and/or based on other information. Alternatively, and/or simultaneously, an arousal metric may be determined based on cortical arousals. Cortical arousals may, for example, be detected using RR intervals. In some embodiments, arousal component 38 may be configured to determine a likelihood of an arousal by subject 12. In some embodiments, arousal component 38 may be configured to determine a level and/or degree of arousal for subject 12. In some embodiments, an arousal metric may be based on the detection of a particular neural state, for example by neural component 30. Other components of system 10 may use or be based on detections and/or determinations by arousal component 38.

Returning to FIG. 1, sleep stage component 36 is configured to determine the current sleep stage of subject 12 based on cardiac parameters, respiratory parameters, output signals from sensors 18, and/or other information. Some embodiments do not require knowledge of the current sleep stage. As described above, the current sleep stage of subject 12 may correspond to one or more of wakefulness, REM sleep, stage N1, stage N2, and/or stage N3 sleep. Sleep stage component 36 is configured to determine whether subject 12 is presently in slow wave sleep. In some embodiments, slow wave sleep and/or slow wave activity may correspond to stage N3 sleep. In some embodiments, stage N2 and/or stage N3 sleep may be slow wave sleep and/or correspond to slow wave activity. By way of non-limiting example, as subject 12 progresses into deeper and deeper stages of sleep, the pulse rate of the subject and/or the pulse rate metric may show a corresponding decrease. Sleep stage component 36 may be configured to determine the current sleep stage based on the decrease in the pulse rate metric. System 10 may control the provision of sensory stimulation based on determinations by one or more components, including, but not limited to, sleep stage component 36.

The parasympathetic nervous system of subject 12 is responsible for regulating activities that occur when the body is at rest. The behavior of the parasympathetic nervous system during sleep is different than the behavior of the parasympathetic nervous system during wakefulness because the level of consciousness during sleep interferes less with ongoing processes in the brain. During sleep, the low frequency oscillations decrease in intensity compared to the wakeful state such that the intensity of the low frequency oscillations is lowest during stage N3 sleep. Sleep stage component 36 may be configured to determine the current sleep stage based on the decrease in the intensity of the low frequency oscillations.

For example, FIG. 5 illustrates high frequency peak 506 to peak 506 oscillation in output signal 500 strength at a frequency of about 1 Hz that corresponds to the pulse rate of a subject (e.g., subject 12). A low frequency oscillation in the range 0.04-0.3 Hz indicated by peak 510 is superimposed on the high frequency oscillation (subsequent peaks 510 are not shown in FIG. 5). The low frequency oscillation is related to the activity of the parasympathetic nervous system. Sleep stage component 36 (FIG. 1) may determine whether the subject is presently in slow wave sleep based at least in part on differences in the intensities of the low frequency oscillations for individual sleep stages.

Figure 6A:
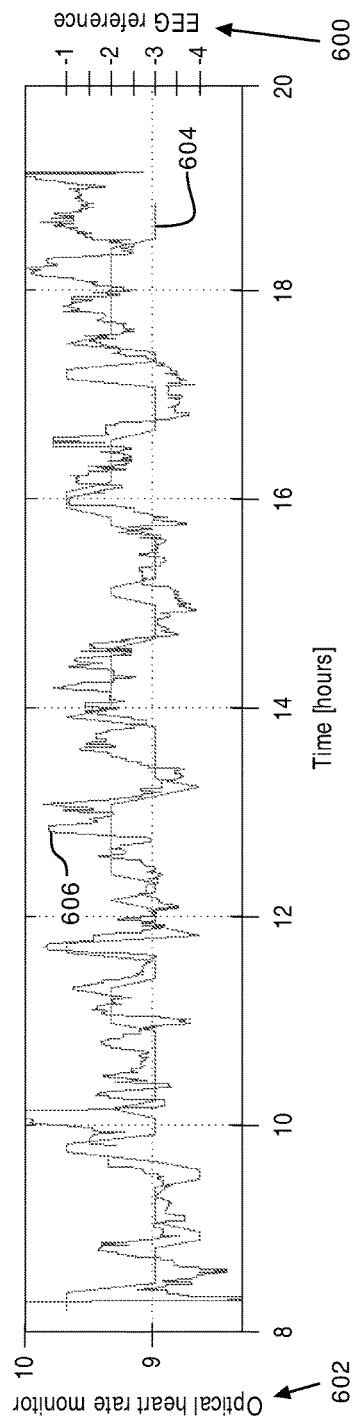
FIG. 6A illustrates an example of a comparison between sleep stages determined from an EEG and the output signals from a sensor in the 0.04-0.30 Hz range.

FIG. 6A illustrates a comparison between sleep stages determined from an EEG 600 and a blood volume metric 602 (e.g., based on the output signals of optical sensor 40 in the 0.04-0.30 Hz range) for a subject. Sleep stage variation over time 604 determined from EEG 600 and variation of the blood volume metric over time 606 generally correlate with each other. The general correlation of sleep stage variation over time 604 and the blood volume metric over time 606 indicates that low frequency oscillations of the blood volume are related to the sleep stage in a subject such that sleep stage component 36 (shown in FIG. 1) may determine the current sleep stage of subject 12 based on the determined blood volume metric and/or the output signals from sensors 18.

Figure 6B:
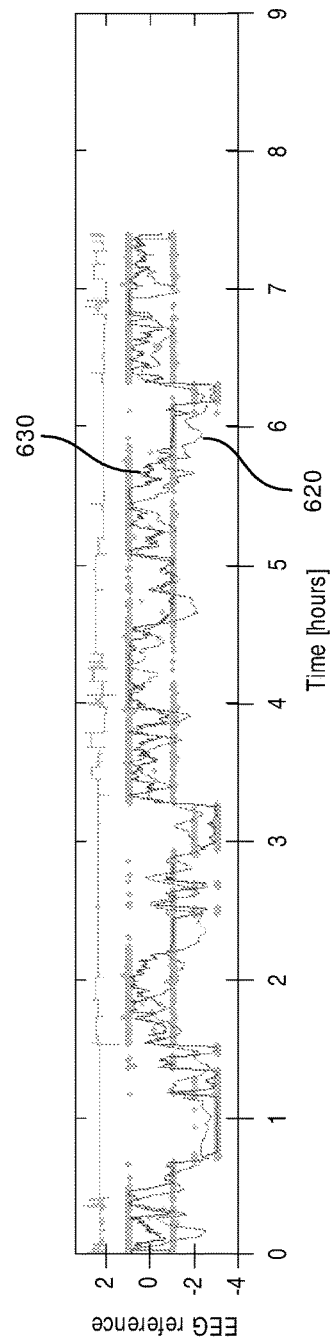
FIG. 6B illustrates that heart rate variability over time generally correlates with sleep stage variation over time such that a sleep stage component may determine the current sleep stage of a subject based on the determined heart rate variability.

Similarly, FIG. 6B illustrates that heart rate variability (the pulse rate metric) 620 over time generally correlates with sleep stage variation 630 over time such that sleep stage component 36 (shown in FIG. 1) may determine the current sleep stage of subject 12 based on the determined heart rate variability. Heart rate variability over time 620 may be determined by parameter component 30. Sleep stage variation over time 630 may be determined via an EEG by using, for example, the heart rate variability information conveyed by the electrocardiogram (ECG) signals.

Control component 34 is configured to control the one or more sensory stimulators to provide the sensory stimuli to the subject to induce, enhance, and/or adjust slow wave activity in the subject, e.g. based on one or more determinations and/or detections by one or more other components of system 10. For example, control component 34 may operate based on determinations by neural component 32 and/or arousal component 38. For example, control component 34 may operate while subject 12 is determined to be in slow wave sleep (e.g., stage N3). In some embodiments, adjusting slow wave activity may include enhancing slow wave activity. In some embodiments, the one or more sensory stimulators are controlled to provide sensory stimuli to the subject to induce sleep slow waves. In some embodiments, the manifestation of induced sleep slow waves may be measured via slow wave activity.

In some embodiments, control component 34 may determine timing for delivery of sensory stimulation. In some embodiments, the timing for delivery of sensory stimulation may correspond to, e.g., the determination that subject 12 is presently in slow wave sleep and/or a target level of neural activity. For example, control component 34 may be configured to determine timing for delivery of sensory stimulation such that auditory stimulation is delivered to subject 12 a predetermined amount of time after sleep stage component 36 determines that subject 12 is presently in sleep stage N3. Control component 34 may be configured to determine a timing for delivery of sensory stimulation such that the determined timing corresponds to sleep stages associated with slow wave activity because the likelihood for slow-wave induction, and/or adjustment during the specific sleep stage may be comparatively higher than in other sleep stages, the user may be less likely to be awakened by the sensory stimuli, and/or for other reasons. In some embodiments, control component 34 is configured to control sensory stimulator 16 to cease providing sensory stimulation to subject 12 responsive to the arousal metric, e.g. as determined by parameter component 30, indicating that subject 12 is waking up.

In some embodiments, control component 34 may be configured to operate by using detections in a feedback manner. In some embodiments, control component 34 may be configured to operate by using detections in an adaptive manner. For example, sensory stimulation may be reduced as more arousals are detected and/or the likelihood of arousals increases. For example, sensory stimulation may be increased as fewer arousals are detected and/or the likelihood of arousals decreases, e.g. throughout a sleep session. In some embodiments, control component 34 may be configured to (adaptively) learn patient-specific characteristics with regard to sensory stimulations and arousals. For example, a particular patient may be sensitive to a particular type and/or characteristics of sensory stimulation, and less sensitive to another type and/or characteristic of sensory stimulation. The different types and/or characteristic may correspond to different sounds, different amplitudes or intensities, different frequencies for sounds used as stimulation, and so forth. Arousal information, e.g. thresholds for different types and/or characteristics of sensory stimulations that may wake up a subject, may be patient-specific. specific. For example, a particular subject may be sensitive to a particular type of visual stimulation. In such a case, control component 34 may be configured to adjust the provided sensory stimulation accordingly (e.g. by reducing and/or avoiding the particular type of visual stimulation) for that particular subject.

In some embodiments, control component 34 may be configured to control sensory stimulator 16 to adjust slow wave activity in subject 12 during the current sleep session. Adjusting slow wave activity in subject 12 while subject 12 is asleep during the current sleep session may include controlling sensory stimulator 16 to increase and/or decrease slow wave activity in subject 12 during sleep. In some embodiments, control component 34 may control sensory stimulator 16, e.g. in a feedback manner, to provide the sensory stimulation during the current sleep session such that the sensory stimulation does not wake subject 12. For example, control component 34 may control sensory stimulator 16 to provide the sensory stimulation at a low intensity level.

In some embodiments, control component 34 may cause information related to the current sleep session of subject 12 to be stored in electronic storage 22. Information related to the current sleep session may include information related to a sleep pressure, slow wave activity induction and/or adjustments, the intensity level of the stimulation, transitions between sleep stages, timing information, information related to the one or more cardiac and/or respiratory parameters, and/or other information.

Electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received from subject 12, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, the cardiac activity parameters may be displayed to a caregiver via user interface 24. As another example, user interface 24 may be configured to receive entry and/or selection of sensor 18 configuration information. The configuration information may allow a user to customize the operation of sensor 18 and/or other aspects of system 10.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with sensory stimulator 16, sensory stimulator 16, and/or other components of system 10. In some embodiments, user interface 24 may include camera 50, for example.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 7:
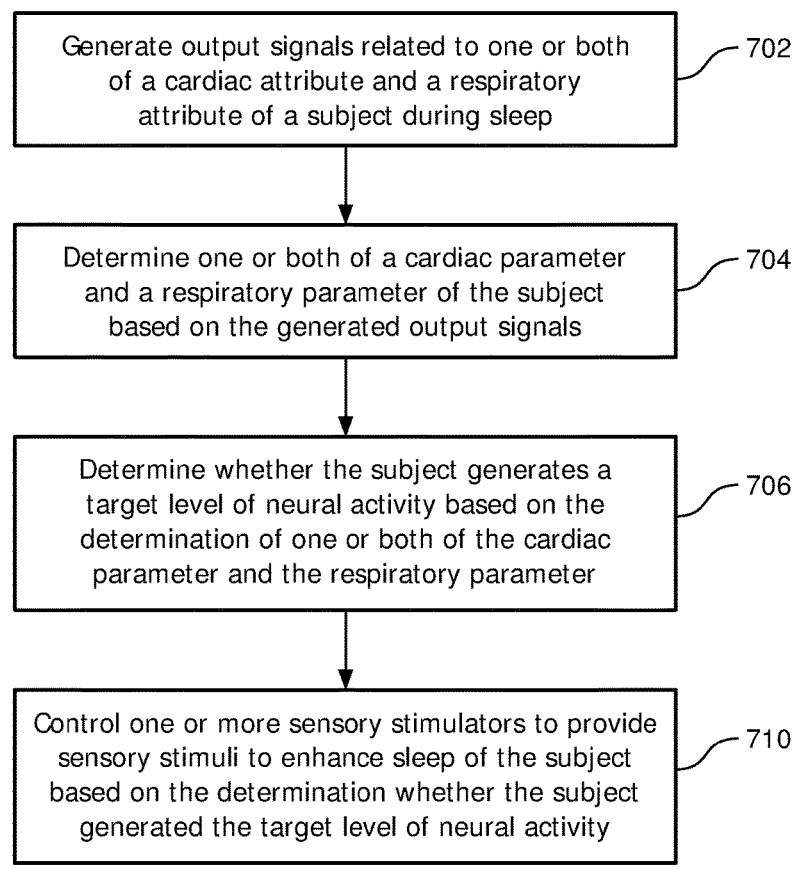
FIG. 7 illustrates a method for managing a current sleep session of a subject with a management system.

FIG. 7 illustrates a method 700 for providing sensory stimuli to enhance sleep of a subject. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, output signals are generated, conveying information related to one or both of a cardiac attribute and a respiratory attribute of the subject during sleep. In some embodiments, operation 702 is performed by one or more sensors the same as or similar to one or more sensors 18 (shown in FIG. 1 and described herein).

At an operation 704, one or both of a cardiac parameter and a respiratory parameter are determined based on the generated output signals. In some embodiments, operation 704 is performed by a parameter component the same as or similar to parameter component 30 (shown in FIG. 1 and described herein).

At an operation 706, it is determined whether the subject generates a target level of neural activity based on the determination of one or both of the cardiac parameter and the respiratory parameter. In some embodiments, operation 706 is performed by a neural component the same as or similar to neural component 32 (shown in FIG. 1 and described herein).

At an operation 708, the one or more sensory stimulators are controlled to provide sensory stimuli to the subject based on the determination whether the subject generates the target level of neural activity. In some embodiments, operation 708 is performed by a control component the same as or similar to control component 34 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to provide sensory stimuli to enhance sleep of a subject, the system comprising:
one or more sensory stimulators configured to provide sensory stimuli to the subject;
one or more sensors configured to generate output signals conveying information related to a cardiac attribute of the subject during sleep; and
one or more processors configured to execute computer program components, the computer program components comprising:
a parameter component configured to determine a cardiac parameter of the subject, wherein such determination is based on the generated output signals from the one or more sensors, and wherein the cardiac parameter is based on cardiac interbeat intervals (IBIs);
a neural component configured to determine whether the subject generates a target level of neural activity based on the cardiac parameter; and
a control component configured to control a timing of delivery of the one or more sensory stimulators to provide the sensory stimuli to enhance sleep of the subject, wherein the timing is based on a criterion associated with the target level of neural activity.

2. The system of claim 1, wherein the target level of neural activity corresponds to a particular sleep stage.

3. The system of claim 1, wherein determinations by the neural component are performed by estimating an intensity of slow wave neural activity of the subject.

4. The system of claim 1, wherein the parameter component is further configured to determine an autonomic parameter based on the generated output signals, wherein the autonomic parameter is related to functioning of an autonomic nervous system of the subject, and wherein determinations by the neural component are further based on the determined autonomic parameter.

5. The system of claim 1, further comprising:
an arousal component configured to detect arousals of the subject,
wherein the control component is configured to adjust provision of the sensory stimuli based in a feedback manner on detections by the arousal component.

6. The system of claim 1, wherein the criterion corresponds to the subject generating the target level of neural activity for a predetermined amount of time.

7. A method for determining whether to provide sensory stimuli to enhance sleep of a subject with a system that includes one or more sensory stimulators, one or more sensors, one or more processors configured to execute computer program components, a parameter component, a neural component, and a control component, the method comprising:

generating, by the one or more sensors, output signals conveying information related to a cardiac attribute of the subject during sleep;

determining, by the parameter component, a cardiac parameter of the subject based on the generated output signals, wherein the cardiac parameter is based on cardiac interbeat intervals (IBIs);

determining, by the neural component, whether the subject generates a target level of neural activity based on the cardiac parameter; and determining by the control component, a timing of delivery of the one or more sensory stimulators to provide sensory stimuli that enhance sleep of the subject, wherein the timing is based on a criterion associated with the target level of neural activity.

8. The method of claim 7, wherein the target level of neural activity corresponds to a particular sleep stage.

9. The method of claim 7, wherein determining whether the subject generates the target level of neural activity includes estimating an intensity of slow wave neural activity of the subject.

10. The method of claim 7, further comprising:

determining an autonomic parameter based on the generated output signals, wherein the autonomic parameter is related to functioning of an autonomic nervous system of the subject, and wherein determining whether the subject generates the target level of neural activity is further based on the autonomic parameter.

11. The method of claim 7, further comprising:

detecting arousals of the subject, and controlling the one or more sensory stimulators based on the detected arousals.

12. A system configured to provide sensory stimuli to enhance sleep of a subject, the system comprising:

means for providing sensory stimuli to the subject;

means for generating output signals conveying information related to a cardiac attribute of the subject during sleep;

first means for determining a cardiac parameter of the subject based on the generated output signals from the means for generating output signals, wherein the cardiac parameter is based on cardiac interbeat intervals (IBIs);

second means for determining whether the subject generates a target level of neural activity based on the cardiac parameter; and means for controlling a timing of delivery of the sensory stimuli to the subject to enhance sleep of the subject, wherein the timing is based on a criterion associated with the target level of neural activity.

13. The system of claim 12, wherein the target level of neutral activity corresponds to a particular sleep stage.

14. The system of claim 12, wherein the second means is configured to estimate an intensity of slow wave neural activity of the subject.

15. The system of claim 12, wherein the first means is further configured to determine an autonomic parameter based on the generated output signals, wherein the autonomic parameter is related to functioning of an autonomic nervous system of the subject, and wherein operation of the second means is further based on the autonomic parameter.

16. The system of claim 12, further comprising:

means for detecting arousals of the subject, wherein the means for controlling the one or more sensory stimulators operates based on the detected arousals.

17. A system configured to provide sensory stimuli to enhance sleep of a. subject, the system comprising:

one or more sensory stimulators configured to provide sensory stimuli to the subject;

one or more sensors configured to generate output signals conveying information related to a cardiac attribute of the subject during sleep; and one or more processors configured to execute computer program components, the computer program components comprising:

a parameter component configured to determine an autonomic parameter based on the generated output signals, wherein the autonomic parameter is related to functioning of an autonomic nervous system of the subject;

a neural component configured to determine whether the subject generates a target level of neural activity based on the determined autonomic parameter, and a control component configured to control the one or more sensory stimulators to provide the sensory stimuli to enhance sleep of the subject, wherein control is based on determinations by the neural component.

* * * * *